US008227191B1

(12) United States Patent
Murakawa et al.

(10) Patent No.: US 8,227,191 B1
(45) Date of Patent: Jul. 24, 2012

(54) METHOD FOR AMPLIFICATION AND DETECTION OF RNA SEQUENCES

(75) Inventors: George J. Murakawa, Cypress, CA (US); R. Bruce Wallace, Pasadena, CA (US); John A. Zaia, Arcadia, CA (US); John J. Rossi, Glendora, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 07/402,450

(22) Filed: Sep. 1, 1989

Related U.S. Application Data

(63) Continuation-in-part of application No. 07/355,296, filed on May 22, 1989, now abandoned, which is a continuation of application No. 06/941,379, filed on Dec. 15, 1986, now abandoned, application No. 07/402,450, which is a continuation-in-part of application No. 07/143,045, filed on Jan. 12, 1988, now abandoned, which is a continuation-in-part of application No. 06/941,379, filed on Dec. 15, 1986, now abandoned, application No. 07/402,450, which is a continuation-in-part of application No. 07/148,959, filed on Jan. 27, 1988, now abandoned.

(51) Int. Cl.
    C12Q 1/68      (2006.01)
    C07H 21/04     (2006.01)
(52) U.S. Cl. .................. 435/6.12; 536/24.31; 536/24.32; 536/24.33
(58) Field of Classification Search .................. 435/6, 91, 435/91.2, 91.21; 436/501, 811; 935/3, 20, 935/77, 78; 536/23.1, 24.31, 24.32, 24.33
See application file for complete search history.

(56) References Cited

U.S. PATENT DOCUMENTS

| | | | | |
|---|---|---|---|---|
| 4,683,195 | A | * | 7/1987 | Mullis et al. ..................... 435/6 |
| 5,008,182 | A | | 4/1991 | Sninsky et al. |
| 5,110,802 | A | | 5/1992 | Cantin et al. |
| 5,110,810 | A | | 5/1992 | Eich et al. |
| 5,176,995 | A | * | 1/1993 | Sninsky et al. ..................... 435/6 |
| 5,219,727 | A | * | 6/1993 | Wang et al. ........................ 435/6 |
| 5,476,774 | A | * | 12/1995 | Wang et al. ..................... 435/91.2 |
| 5,622,820 | A | * | 4/1997 | Rossi ................................. 435/5 |
| 5,783,391 | A | | 7/1998 | Rossi |
| 5,869,249 | A | | 2/1999 | Rossi |

OTHER PUBLICATIONS

Wathen et al. J. Virol 41(2):462 (1982).*
Demaechi. Virol. 114:23- (1981).*
Ratner et al. Nature 313(2):277 (1985).*
Starcich et al. Science 229:537 (1985).*
Rüger et al. J. of Virol 61(2):446 (1987).*
Akusjärvi et al P.N.A.S. 75(12):5822 (1978).*
Hennighausen et al. EMBO J. 5(6):1367 (1986).*
Harper et al. PNAS 83:772 (1986).*
Stratagene 1988 Catalog [Published by Stratagene, 11011 North Torrey Pines Road, La Jolla, CA, USA], p. 39, 1988.*
Diaco, PCR Strategies, ed. Innis et al., Academic Press, Inc., ch. 7, pp. 84-108 (1995).*
Slamon, et al., "Expression of Cellular Oncogenes in Human Malignancies" *Science* 224:256-262 (1984).
Kraus, et al., "Overexpression of the EGF receptor-related proto-oncogene erbB-2 in human mammary turmor cell lines by different molecular mechanisma", *The EMBO Journal* 6(3):605-610 (1987).
Chelly, et al., "Transcription of the dystrophin gene in human muscle and non-muscle tissues" *Nature* 333:858-860 (1988).
S.K. Arya, 3'-*orf* and *sor* genes of human immunodeficiency virus: In vitro transcription-translation and immunoreactive domains, Proc. Natl. Acad. Sci., vol. 84, Aug. 1987, pp. 5429-5433.
F. Zhang, "Fine-Structure Analysis of the Processing and Polyadenylation Region of the Herpes Simplex Virus Type 1 Thymidine Kinase Gene by Using Linker Scanning, Internal Deletion, and Insertion Mutations," Molecular and Cellular Biology, vol. 6, No. 12, Dec. 1986, pp. 4611-4623.
G. J. Murakawa, et al., "Laboratory Methods: Direct Detection of HIV-1 RNA from AIDS and ARC Patient Samples," DNA, vol. 7, No. 4, 1988, pp. 287-295.
J. A. Zaia, M.D. et al., "Confirmation of HIV Infection Using Gene Amplification," Testtrends, vol. 3, No. 1, Jun. 1989, pp. 4-5.
J.A. Zaia, "Confirmation of HIV Infection Using Gene Amplification," Transfusion Medicine Reviews, vol. 3, No. 1, Suppl. 1, Jan. 1989, pp. 27-30.

* cited by examiner

*Primary Examiner* — Prabha Chunduru
(74) *Attorney, Agent, or Firm* — Rothwell, Figg, Ernst & Manbeck PC

(57) ABSTRACT

A process for identifying a viral RNA nucleotide sequence present in a sample of peripheral blood cells which comprises amplifying such RNA simultaneously with at least one other RNA nucleotide sequence present in a virus infected cell in said sample, and thereafter separately and sequentially analyzing the amplification reaction products with probes homologous with authentic RNA and with such other RNA sequence to identify one or both of said RNA nucleotide sequences.

47 Claims, No Drawings

METHOD FOR AMPLIFICATION AND DETECTION OF RNA SEQUENCES

This application is a continuation-in-part of each of application Ser. No. 07/355,296 filed May 22, 1989, now abandoned (which is a file-wrapper-continuation of application Ser. No. 06/941,379, filed Dec. 15, 1986) now abandoned application Ser. No. 07/143,045 filed Jan. 12, 1988 now abandoned (which is a continuation-in-part of application Ser. No. 06/941,379), now abandoned and application Ser. No. 07/148,959 filed Jan. 27, 1988 now abandoned application Ser. Nos. 07/355,296, 07/143,045 and 07/148,959 are incorporated in this application by reference.

This invention was made with government support under Grant Nos. U01 CA34991 and P01 CA30206 awarded by the National Institutes of Health. The government has certain rights in the invention.

BACKGROUND

It is known to utilize the polymerase chain reaction (PCR) to amplify RNA and DNA sequences present in small samples. The amplification procedure can be simultaneously performed on more than one sequence. The presence or absence of a specific sequence in the amplification product may be determined by oligonucleotide hybridization assays. See generally Mullis, U.S. Pat. No. 4,683,195.

Virus etiology generally and retrovirus etiology in particular are complex. See Varmus, Retroviruses, *Science* 240: 1427-1435 (1988). Known PCR techniques, as applied to rapidly diagnose or confirm potential retroviral positive patients, are of limited sensitivity, lack positive controls and may otherwise be unreliable. For example, persons who were seropositive but both virus culture-negative and PCR-negative are reported by Ou et al. *Science* 239:295-297 (1988). As a first explanation for this observation, Ou suggests that these persons may have contained an insufficient number of provirus copies to be directly detected by the PCR technique utilized.

SUMMARY OF THE INVENTION

This invention provides a PCR technique of improved sensitivity which includes a positive control for determination of the presence or absence of a target sequence in viral RNA sample.

Increased sensitivity is provided by utilizing viral RNA as the original PCR template. The viral RNA is converted to complementary DNA which is then amplified. Unique sequences in samples containing as few as 100 molecules of RNA and retroviral RNA in samples from as little as 10 nanograms (ng) of total cellular RNA can be detected by the invention. Positive controls are provided by amplification of at least one synthetic RNA sequence simultaneously with the RNA sample.

Clinical applications of the invention include the identification and quantification of viral RNA present in peripheral blood samples and laboratory cell lines. Patients who harbor a viral genome but are not yet producing anti-viral antibodies may be diagnosed as uninfected by known screening methods. In contrast, this invention enables detection of viral transcripts, such as those of the AIDS virus which may accumulate in the absence of viral protein translation during the early stages of infection.

DETAILED DESCRIPTION OF THE INVENTION

In general the method of the invention entails utilizing a sample RNA which has or may have a target viral sequence as a template for amplification by PCR. A first oligonucleotide primer for the target viral sequence is annealed to the template for extension through the target sequence to produce a first extension product having an RNA template strand and a DNA primer extension strand. The first extension product is denatured and the separated RNA template and DNA primer extension strands are annealed, respectively to the first primer and to a second primer complementary to the DNA primer extension strand. The first and second primers are positioned for extension through the target sequence on the template and its complement on the primer extension strand. The first and second primers are extended to produce a second primer extension product which is denatured, the first and second primers are again annealed to the separated template and primer extension strands, and again extended and the resulting extension products denatured. The process is repeated for the number of cycles deemed appropriate to achieve the desired degree of amplification.

After the final round of amplification and denaturation, the product is analyzed, for example, by oligonucleotide hybridization assay to determine the presence or absence of a sequence indicative of the presence of the target sequence in the sample.

In the early cycles, e.g., the first five cycles after the production and denaturing of the first extension product, the amplification steps are conducted in the presence of both reverse transcriptase and the large fragment of DNA polymerase I (Klenow) or similarly functioning enzyme. Subsequent cycles may appropriately be conducted in the absence of reverse transcriptase. Ribonuclease A is preferably added after about 5 to about 7 cycles of DNA amplification to destroy residual RNA and reduce sequence complexity of the mixture.

In the preferred practice of the invention, both the first and second primer are present throughout the amplification procedure. Alternatively the second primer can be added at any stage of the process prior to the amplification of the denatured first extension product.

For identification and quantification purposes it is preferred to amplify the viral RNA sample, typically from virus infected T-4 lymphocytes present in peripheral blood, simultaneously with at least one other RNA sequence to provide a positive control and reduce the risk of false negative data. A plurality of first and second primer pairs is provided, one such pair for each RNA sequence to be amplified. The amplification procedure is otherwise accomplished as previously described.

The T-4 lymphocyte cell population which is primarily infected by a virus expresses the T-cell receptor. Hence sequences unique to the T-cell receptor provide appropriate positive control sequences useful in the invention. Although other such unique sequences may be selected, at least a portion of the constant region of the relevant T-cell receptor β chain is preferred for use as a control sequence.

Additional control sequences include those which are present in the expression products of all or virtually all of the cells of a patient sample even when the T-cell count is low or which can be amplified and detected by the same oligonucleotide as those used for authentic virus RNA samples.

Primers useful for the amplification of HIV-1 sequences include:

| Sequence | Location | |
| --- | --- | --- |
| 5' LTR | 88-284 | (Starcich, et. al. *Science* 227: 538-540 (1985)) |
| gag | 1551-1665 | (Ratner, et al. *Nature* 313: 277-284 (1985)) |
| env | 7801-9081 | (Ratner, et al. *Nature* 313: 277-284 (1985)) |
| 3'ORF (nef) | 8950-9081 | (Ratner, et al. *Nature* 313: 277-284 (1985)) |

Specifically preferred first and second HIV-1 primers and a useful probe when the target is the 3' ORF (nef) sequence comprising the following synthetic oligonucleotides:

```
HIVA:     5' ATG CCG ATT GTG CTT GGC TA 3' or
          5' ATG CTG ATT GTG CCT GGC TA 3'

HIVB:     5' TGA ATT AGC CCT TCC AGT CC 3'

HIVC (PROBE):
          5' AAG TGG CTA AGA TCT ACA GCT GCC T 3'
```

When the target is the HIV-1 5' LTR sequence the following primer and probe sequences are appropriate:

```
HIVD Primer:
      5' TGA GTG CTT CAA GTA AGTG TGT GCC C 3'

HIVE Primer:
      5' GTC GCC GCC CCT CGC CTC TTG CCG T 3'

HIVF Probe:
      5' CGA AAG GGA AAC CAG AGC TCT CTC G 3'
```

As applied to human cytomegalovirus (HCMV), a target for amplification is a region of the HCMV major IE gene (IE1) region between nucleotides 1154 and 1331. Oligodeoxyribonucleotides complementary to sequences in this region are used with RNA from HCMV infected cells, or from patient peripheral blood samples. Suitable oligonucleotide primers and probes have the following sequences:

| HCMV | 1154 5' CGAGACACCCGTGACCAAGG 3' 1173 |
| --- | --- |
| HCMVB | 1311 3' CTCTTTCTACAGGACCGTCT 5' 1330 |
| HCMV (Probe I) | 1182 3' AAGGACGTCTGATACAACTCCTT 5' 1204 |

An additional amplification system is needed for detection of RNA from the transcripts of late HCMV genes, which are important markers for active infection. For this purpose, sequences 866-1025 from the coding sequence of p64 (see, Ruger, B., et al. *J. Virol.* 61:446 (1987)) may be amplified. Suitable oligonucleotide primers and probes have the following sequences:

| HCMVD | 866 5' AAAGAGCCCGACGTCTACTACACGT 3' 890 |
| --- | --- |
| HCMVE | 1001 3' CTGGTCATGCAGTTCCACATGGACC 5' 1025 |
| HCMV Probe II | 941 3' CGCGTGCTCGACCAAACGAGGTACCTCTTG 5' 970 |

When the T-cell receptor ps chain is used to provide a construct, appropriate primers and probes may have the sequences:

```
Primer A:  5' GTC CAC TCG TCA TTC TCC GA 3' or
           5' GTC CAC TCG TCA TTC TCC GAG 3'

Primer B:  5' TCA AGA CTC CAG ATA CTG CCT 3' or
           5' TAA TAC GAC TCA TAT AGG GAC TCC AGA
              TTA CGC CTG AGC 3'

Probe C:   5' CAG AAG GTG GCC GAG ACC CTC AGG C 3'
           or
           5' CAG AAG GTG GCC GAG ACC CTC CGG C 3'
```

Sequences unique to β-actin tend to be ubiquitously present in the expression products of all of the cells of the patient sample and hence provide useful controls. Preferred synthetic oligonucleotide primer and probe sequences for use in connection with β-actin controls are:

```
Primer A:  5' CTC ATT GCC AAT GGT GAT GAC CTG 3'

Primer B:  5' GCT ATC CCT GTA CGC CTC TGG C' or
           5' GCT ATC CCT GTA CGC CTC ACC G'

Probe C:   5' CGG TGA GGA TCT TCA TGA GGT AGT C' 3'
           or
           5' CGG TGA GGA TCT TCA TGA GCT AGT C 3'
```

An additional aid to quantitation of virus levels in patient samples is provided by a reference RNA which can be amplified and detected by the same oligonucleotides used for authentic virus RNA samples.

Such a reference RNA may be a "minigene" or a "maxigene" formed by a multi-base pair insert into or deletion of at least about 20 nucleotides from a unique site. For example a preferred reference RNA includes a 21 base pair insert into the KpnI site of the HIV-1 3' ORF (nef) region of the pGEM92 clone described in Example I. An insert of sequence:

5'CACACAAGGCTACTTCGGTAC 3',
3'GTGTGTTCCGATGAAGCCATG5' is appropriate.

The transcription product of this clone is 21 bases longer than the authentic HIV-sequence but still hybridizes with the 25-mer probe HIVC. It is therefore distinguishable by size from the authentic viral product.

Such "minigenes" and "maxigenes" not only provide an internal control but also an additional aid to quantitation. Because the quantity of "maxigene" minigene RNA originally included in the amplification reaction is known, the amount of signal obtained from the maxi or minigene amplification product can be related to the signal obtained from the patient sample. Hence, the relative quantitation of the original amount of authentic HIV-1 in the patient sample is provided.

Similar procedures can be used as a quantitative assay of HCMV sequences. A segment of the cDNA derived from the major IE gene IE1 is subcloned into the transcription vector pTZ18U (BioRad), and includes nucleotides 1185-1331. A small insertion accomplished either by cloning or by site directed mutagenesis is made in this segment which permits distinction between the PCR-amplified viral RNA and cellular amplified transcripts. By including a fixed amount of this plasmid HCMV RNA or DNA in every sample to be amplified, it is possible to measure the amount of viral DNA or RNA using the in vitro sample as an internal standard.

To provide appropriate signals either the primers or the probes are labelled, e.g., with an isotope such as $p^{32}$ or a fluorophore. Preferably, the probes are labelled.

For purposes of identification and quantification, the amplification products may be electrophoresed in a gel, e.g., agarose or 6% polyacrylamide, 7 M. urea gel. Labelled probes complementary to each of the amplified sequences are used sequentially. Hybridization of the probes with amplification products other than of authentic viral sequence, e.g., HIV or HCMV provides positive controls thus minimizing the possibility of false negative data regarding the authenticity of the original sample. More particularly, if the authentic, e.g., HIV probe yields negative data, but one or both the T-cell receptor and beta actin probes yield positive data, the conclusion may be feasibly drawn that the original sample was viable notwithstanding the negative HIV probe result. Thus, the invention includes a process for discerning false negative data or positive data in the identification of a target viral RNA sequence in a peripheral blood cell sample which process comprises:

(i) selecting said target viral RNA sequence;
(ii) simultaneously subjecting
   (a) said sample and
   (b) at least one synthetic RNA reference sequence which does not include said target sequence or which includes substantially more nucleotides than said target sequence or which includes at least about 20 nucleotides less than said target sequence
   to polymerase chain reaction amplification under conditions appropriate to simultaneously amplify said target sequence if present in said sample and said reference sequence;
(iii) denaturing the amplification product or products produced by step (ii);
(iv) subjecting said denatured amplification product or products of step (iii) to hybridization conditions separately and sequentially with probes homologous to said target sequence and to said reference sequence,
   each of said probes being removed from a sequence with which it is hybridized prior to the separate and sequential subjection of said amplification products to hybridization with another of said probes;
(v) determining whether said amplified target and reference sequences are hybridized with said probes homologous therewith, false negative data being indicated by failure of said probes to hybridize either to the sample or to the reference sequence and false positive data being indicated by hybridization of the target sequence probe and by the absence of hybridization of the reference sequence probe.

The process of the invention is useful to amplify and detect viral RNA from any source. It has particular application to the detection and quantification of AIDS (HIV-1) virus and cytomegalovirus (HCMV).

Example I

This example illustrates the amplification of in vitro synthesized RNA by the use of the plasmid pSP64-BH10-R3 (Biotech Research Laboratories, Inc.), containing the entire HTLV-III (HIV-1) virus excluding the LTRs, as the starting material for the following subclone vectors. A 1.1 kb BamHI restriction fragment including HIV-1 sequences 8052 to 9149 was subcloned in both orientations into the BamHI site of the transcription vector pGEM2 (Promega Biotec). The resulting plasmids, pGM92 (+strand) and pGM93 (− strand), were digested with EcoR1 and transcribed with T7 RNA polymerase using a T7 transcription kit (BioRad Laboratories, Inc.).

$10^{-1}$ pmol of RNA from pGM92 was subjected to 4, 5, 8 and 10 cycles of amplification. Amplification was performed using I-X amplification buffer (10 mM tris-HCl, pH 7.5; 10 mM $MgCl_2$; 66 mM NaCl; 1 mM dithiothreitol), 1.5 mM of each dNTP, and 1.0 uM of each oligodeoxyribonucleotide (HIVA and HIVB, supra) in a final reaction volume of 100 ul. Samples were denatured by heating to 95° C. for 2 minutes, spun in a microfuge for 5 seconds, cooled to 37° C. for 2 minutes, at which time 1.0 ul of reverse transcriptase (2.0 units, BioRad), diluted in amplification buffer, was added for 2 minutes. Cycles 2-5 were performed as described above, except both reverse transcriptase and Klenow (0.5 units, Boehringer Mannheim) were added. In cycle 6, RNase A was added (0.45 ug) and only DNA pol I was used. All subsequent cycles of amplification were performed with only the presence of DNA pol I. After completion of the last cycle of amplification, samples were placed on ice and a 10.0 ul portion was electrophoresed in a 1.8% agarose gel. The DNA was transferred to Zeta probe (BioRad) using an alkaline blotting procedure (see Reed, K. G., et al. *Nucleic Acids Res.* 13:7207-7221 (1988)) and prehybridized and hybridized as follows: The prehybridization reaction was performed at 65° C. for 1 to 3 hours in 20 ml of 6×SSPE (1.0 M NaCl, 0.06 M $NaPO_4$, 0.006 M EDTA); 1.0% SDS; 0.5% rehydrated, powder skim milk; and 10 ug per ml of sonicated, denatured salmon sperm DNA. The hybridization reaction was in 20 ml of the same buffer, except the salmon sperm DNA was omitted and replaced with 20 pmol of 5'-$^{32}$P-labelled oligodeoxyribonucleotide probe HIVC (ca. $3 \times 10^8$ cpm). Hybridization was for 1 hour to overnight at 65° C. The hybridized filter was washed with three 250 ml volumes of 6×SSC (0.95 M NaCl, 0.095 M Na Citrate), 0.1% SDS at 65° C. for 5 minutes each, and autoradiographed at −70° C. for 1 hour on Kodak XAR-5 film with an intensifying screen.

A 3.81 fold level of amplification was revealed by densitometric scanning and integration of the peak areas. Thus, if 21 cycles were performed with this template, and since only one strand is synthesized during the first cycle, the calculated theoretical amplification is over 400,000 fold.

Example II

To test the sensitivity of amplification, samples in which $10^{-9}$, $10^{-7}$, and $10^{-5}$, pmol of pGM92 RNA were used in repetitions of Example I. After 21 cycles of replication, bands from each of the samples could be detected after Southern blot hybridization. Since only one tenth of the reaction was used in the detection of the positive sequence in a sample from only $10^{-9}$ pmol, this result shows that as few as 100 molecules of RNA are sufficient for detection after amplification.

Example III

This example demonstrates amplification of an RNA template in the presence of non-specific RNA. 5.5 ug of bovine rRNA was added to a reaction mixture as described in Example I containing $10^{-3}$ pmol of GM92 RNA. Specific amplification was seen at high efficiency.

Example IV

This example demonstrates that RNA isolated from HIV infected cells can be efficiently utilized for amplification and detection pursuant to this invention. Polymerase chain reaction using only 10 ng of total RNA from HIV infected H9 cells was performed as described in Example I. A specific hybridizing band, about two orders of magnitude lower than the 1.0 ug sample, was observed. To test if the amplification of the in vivo sample was from RNA or residual DNA contamination, a control sample in which RNase A was added prior to amplification was examined. In this experiment, no hybridization band was detected after prolonged autoradiographic exposure.

Amplification using an oligonucleotide primer containing the T-7 RNA polymerase (BioRad Laboratories) increases the sensitivity of detection when the amplification is followed by a transcription step. The following HIV T7 sequence is illustrative:

HIV T7-5'TTAATACGACTCACTATAGGG 3'.

Example V

Amplification is performed using 1-X amplification buffer (10 mM Tris-HCl, pH 7.5; 10 mM $MgCl_2$; 66 mM NaCl; 1 mM dithiothreitol), 1.5 mM of each dNIP). To this buffer, about 1 mM total peripheral blood lymphocyte RNA from an AIDS infected patient in about 1.0 mM of each of the priming nucleotides HIVA, HIVB T-cell receptor A and T-cell receptor B are added providing a final reaction volume of approximately 100 μl. The sample is heated at 95° C. for 2 minutes, centrifuged for 5 seconds, cooled to 37° C. for about 2 minutes at which time 1.0 μl of AMV reverse transcriptase (Life Sciences or BioRad Laboratories) diluted in the amplification buffer were added and incubation was continued for 2 minutes at 37° C. A second amplification cycle was performed in like manner. Thereafter the final 28 rounds of amplification were accomplished using a buffer consisting of 2.5 units of Thermus aquatus DNA polymerase (Perkin-Elmer Cetus or New England Biolabs): 50 mM KC1, 10 mM Tris, pH 8.3, 1.5 mM $MgCl_2$, 0.01% gelatin, 200 μM each dNTP, and 50 pmoles of each primer in a final volume of 50 microliters overlain with 10 microliters of paraffin oil. The polymerizations are carried out from 1 to 2 minutes at 65° C., with 1 minute of denaturation at 95° C., and 1 minute of annealing at 37° C.

After completion of the last cycle of amplification, the products are placed on ice and a 10 μl portion was electrophoresed in a 1.8% agarose gel. The DNA was transferred to Zeta probe (BioRad) using an alkaline blotting procedure and prehybridized and hybridized as follows: The prehybridization reaction was performed at 65° C. for 1 to 3 hours in 20 ml of 6×SSPE (1.0 M NaCl, 0.06 $NaPO_4$, 0.006 M EDTA); 1.0% SDS; 0.5% rehydrated, powder skim milk (Alba); and 10 μg per ml of sonicated, denatured salmon sperm DNA. The hybridization reaction was in 20 ml of the same buffer, except the salmon sperm DNA was omitted and replaced with 20 pmol of 5'-$^{32}$P-labelled oligodeoxyribonucleotide HIVC (ca. 3×10$^8$ cpm). Hybridization was for 1 hour to overnight at 65° C. The hybridized filter was washed with three 250 ml volumes of 6×SSC (0.95 M NaCl, 0.095 M Na Citrate), 0.1% SDS at 65° C. for 5 minutes each, and autoradiographed at −70° C. for 1 hour on Kodak XAR-5 film with an intensifying screen.

Each of the HIVC and T-cell receptor C probes is used separately and sequentially. After the results with the HIVC probe are obtained, that probe is stripped from the filter by treatment with 100 C 0.1×SSC, 0.1% SDS, two times for 15 minutes each. The filter is then rehybridized to the T-cell receptor C probe.

Bands from each of the authentic HIV and T-cell receptor samples are detected after Southern Blot hybridization.

Example VI

Example I is repeated with the exception that the primer pair beta actin A and beta actin B is included in the amplification reaction mixture.

The amplification products are analyzed separately and sequentially by probes which hybridize with authentic viral RNA, the amplified T-cell receptor RNA sequence and the amplified beta actin A sequence. Bands from each such sequence are detected after Southern blot hybridization.

Example VII

Example I is repeated with the exception that the maxigene primer is included in the reaction mixture.

Kits contemplated by the invention include self-contained appropriate quantities of primers and probes for use in the practice of the invention.

A typical kit for the detection and quantification of HIV-1 virus in a patient peripheral blood sample includes vials or similar separate containers filled with, for example, 20 picomoles/microliters (in sterile $H_2O$) each of HIVA, HIVB or HIVC. A reference RNA (~10,000 copies/microliter) is prepared in sterile DEPC treated water. Such kits include reagents and instructions necessary to conduct the appropriate amplification and hybridization procedures.

We claim:

1. A process for amplification of a target viral RNA and a reference RNA in a sample which comprises:
   (i) selecting a sequence present in the target viral RNA;
   (ii) adding a known quantity of a reference RNA sequence to the sample, wherein the reference RNA sequence comprises a sequence present in the selected target viral RNA sequence and a sequence not present in the selected target viral RNA sequence, wherein the reference RNA sequence and the selected target viral RNA sequence can be amplified by different oligonucleotides and wherein following amplification amplified reference RNA sequence and amplified selected target viral RNA sequence are distinguishable by size or by probes;
   (iii) simultaneously subjecting the selected target viral RNA sequence and the reference RNA sequence in the sample to polymerase chain reaction amplification under conditions appropriate to simultaneously amplify the selected target viral RNA sequence if present in the sample and the reference RNA sequence; and
   (iv) measuring the amounts of the amplified selected target viral RNA sequence and the amplified reference RNA sequence.

2. The process of claim 1, wherein the reference RNA sequence consists of a linear arrangement of a sequence present in the selected target viral RNA sequence, a sequence not present in the selected target viral RNA sequence and a sequence present in the selected target viral RNA sequence.

3. The process of claim 1, wherein the target viral RNA sequence is a human immunodeficiency virus (HIV) RNA sequence or a human cytomegalovirus (HCMV) RNA sequence.

4. The process of claim 1, wherein a primer utilized in the polymerase chain reaction amplification includes a T-7 RNA polymerase binding sequence.

5. The process of claim 1, wherein the amount of the amplified target viral RNA sequence and the amount of the amplified reference RNA sequence are measured by measuring (i) the amount of signal obtained from the amplified target viral RNA sequence and (ii) the amount of signal obtained from the amplified reference RNA sequence.

6. The process of claim 5, wherein the amounts of the signals are determined by the use of labeled probes.

7. The process of claim 6, wherein the label is an isotope or a fluorophore.

8. The process of claim 5, wherein the amounts of the signals are determined by the use of labeled primers in the polymerase chain reaction.

9. The process of claim 8, wherein the label is an isotope or a fluorophore.

10. A process for amplification of a target viral RNA and a reference RNA in a sample which comprises:
(i) selecting a sequence present in the target viral RNA;
(ii) adding a known quantity of a reference RNA sequence to the sample, wherein the reference RNA sequence comprises a sequence present in the selected target viral RNA sequence and a sequence not present in the selected target viral RNA sequence, wherein the reference RNA sequence and the selected target viral RNA sequence can be amplified by different oligonucleotides and wherein following amplification amplified reference RNA sequence and amplified selected target viral RNA sequence are distinguishable by size or by probes;
(iii) simultaneously subjecting the selected target viral RNA sequence and the reference RNA sequence in the sample first to a reverse transcription reaction and then to polymerase chain reaction amplification under conditions appropriate to simultaneously amplify the selected target viral RNA sequence if present in the sample and the reference RNA sequence;
(iv) measuring the amounts of the amplified selected target viral RNA sequence and the amplified reference RNA sequence.

11. The process of claim 10, wherein the reference RNA sequence consists of a linear arrangement of a sequence present in the selected target viral RNA sequence, a sequence not present in the selected target viral RNA sequence and a sequence present in the selected target viral RNA sequence.

12. The process of claim 10, wherein the target viral RNA sequence is a human immunodeficiency virus (HIV) RNA sequence or a human cytomegalovirus (HCMV) RNA sequence.

13. The process of claim 10, wherein a primer utilized in the polymerase chain reaction amplification includes a T-7 RNA polymerase binding sequence.

14. The process of claim 10, wherein the amount of the amplified target viral RNA sequence and the amount of the amplified reference RNA sequence are measured by measuring (i) the amount of signal obtained from the amplified target viral RNA sequence and (ii) the amount of signal obtained from the amplified reference RNA sequence.

15. The process of claim 14, wherein the amounts of the signals are determined by the use of labeled probes.

16. The process of claim 15, wherein the label is an isotope or a fluorophore.

17. The process of claim 14, wherein the amounts of the signals are determined by the use of labeled primers in the polymerase chain reaction.

18. The process of claim 17, wherein the label is an isotope or a fluorophore.

19. A process for amplification of a target viral RNA sequence and a reference RNA sequence in a sample which comprises:
combining a known quantity of a reference RNA sequence with the sample, wherein the reference RNA sequence comprises a sequence present in the target viral RNA sequence and a sequence not present in the target viral RNA sequence, wherein the reference RNA sequence and the target viral RNA sequence can be amplified by different oligonucleotides and wherein following amplification amplified reference RNA sequence and amplified target viral RNA sequence are distinguishable by size or by probes;
simultaneously subjecting the target viral RNA sequence and the reference RNA sequence to polymerase chain reaction amplification under conditions appropriate to simultaneously amplify the target viral RNA sequence and the reference RNA sequence;
measuring the amounts of amplified target viral RNA sequence and amplified reference RNA sequence.

20. The process of claim 19, wherein the reference RNA sequence consists of a linear arrangement of a sequence present in the target viral RNA sequence, a sequence not present in the target viral RNA sequence and a sequence present in the target viral RNA sequence.

21. The process of claim 19, wherein the target viral RNA sequence is a human immunodeficiency virus (HIV) RNA sequence or a human cytomegalovirus (HCMV) RNA sequence.

22. The process of claim 19, wherein a primer utilized in the polymerase chain reaction amplification includes a T-7 RNA polymerase binding sequence.

23. The process of claim 19, wherein the amount of the amplified target viral RNA sequence and the amount of the amplified reference RNA sequence are measured by measuring (i) the amount of signal obtained from the amplified target viral RNA sequence and (ii) the amount of signal obtained from the amplified reference RNA sequence.

24. The process of claim 23, wherein the amounts of the signals are determined by the use of labeled probes.

25. The process of claim 24, wherein the label is an isotope or a fluorophore.

26. The process of claim 23, wherein the amounts of the signals are determined by the use of labeled primers in the polymerase chain reaction.

27. The process of claim 26, wherein the label is an isotope or a fluorophore.

28. A process for amplification of a target viral RNA sequence and a reference RNA sequence in a sample which comprises:
combining a known quantity of a reference RNA sequence with the sample, wherein the reference RNA sequence comprises a sequence present in the target viral RNA sequence and a sequence not present in the target viral RNA sequence, wherein the reference RNA sequence and the target viral RNA sequence can be amplified by different oligonucleotides and wherein following amplification amplified reference RNA sequence and amplified target viral RNA sequence are distinguishable by size or by probes;
simultaneously subjecting the target viral RNA sequence and the reference RNA sequence in the sample first to a reverse transcription reaction and then to polymerase chain reaction amplification under conditions appropriate to simultaneously amplify the target viral RNA sequence if present in the sample and the reference RNA sequence;
measuring the amounts of amplified target viral RNA sequence and amplified reference RNA sequence.

29. The process of claim 28, wherein the reference RNA sequence consists of a linear arrangement of a sequence present in the target viral RNA sequence, a sequence not present in the target viral RNA sequence and a sequence present in the target viral RNA sequence.

30. The process of claim 28, wherein the target viral RNA sequence is a human immunodeficiency virus (HIV) RNA sequence or a human cytomegalovirus (HCMV) RNA sequence.

31. The process of claim 28, wherein a primer utilized in the polymerase chain reaction amplification includes a T-7 RNA polymerase binding sequence.

32. The process of claim 28, wherein the amount of the amplified target viral RNA sequence and the amount of the amplified reference RNA sequence are measured by measuring (i) the amount of signal obtained from the amplified target viral RNA sequence and (ii) the amount of signal obtained from the amplified reference RNA sequence.

33. The process of claim 32, wherein the amounts of the signals are determined by the use of labeled probes.

34. The process of claim 33, wherein the label is an isotope or a fluorophore.

35. The process of claim 32, wherein the amounts of the signals are determined by the use of labeled primers in the polymerase chain reaction.

36. The process of claim 35, wherein the label is an isotope or a fluorophore.

37. The process of claim 1, wherein the sequence not present in the selected target viral RNA sequence is about 21 nucleotides in length.

38. The process of claim 10, wherein the sequence not present in the selected target viral RNA sequence is about 21 nucleotides in length.

39. The process of claim 19, wherein the sequence not present in the selected target viral RNA sequence is about 21 nucleotides in length.

40. The process of claim 28, wherein the sequence not present in the selected target viral RNA sequence is about 21 nucleotides in length.

41. A process for quantitation of a target viral RNA in a sample which comprises:
   (i) selecting a sequence present in the target viral RNA;
   (ii) adding a known quantity of a reference RNA sequence to the sample, wherein the reference RNA sequence comprises a sequence present in the selected target viral RNA sequence and a sequence not present in the selected target viral RNA sequence, wherein the reference RNA sequence and the selected target viral RNA sequence can be amplified by different oligonucleotides and wherein following amplification amplified reference RNA sequence and amplified selected target viral RNA sequence are distinguishable by size or by probes;
   (iii) simultaneously subjecting the selected target viral RNA sequence and the reference RNA sequence in the sample to polymerase chain reaction amplification under conditions appropriate to simultaneously amplify the selected target viral RNA sequence if present in the sample and the reference RNA sequence;
   (iv) measuring the amounts of the amplified selected target viral RNA sequence and the amplified reference RNA sequence; and
   (v) determining the relative amount of the target viral RNA present in the sample before amplification from the amount of the amplified selected target viral RNA sequence and the amount of the amplified reference RNA sequence.

42. A process for quantitation of a target viral RNA in a sample which comprises:
   (i) selecting a sequence present in the target viral RNA;
   (ii) adding a known quantity of a reference RNA sequence to the sample, wherein the reference RNA sequence comprises a sequence present in the selected target viral RNA sequence and a sequence not present in the selected target viral RNA sequence, wherein the reference RNA sequence and the selected target viral RNA sequence can be amplified by different oligonucleotides and wherein following amplification amplified reference RNA sequence and amplified selected target viral RNA sequence are distinguishable by size or by probes;
   (iii) simultaneously subjecting the selected target viral RNA sequence and the reference RNA sequence in the sample first to a reverse transcription reaction and then to polymerase chain reaction amplification under conditions appropriate to simultaneously amplify the selected target viral RNA sequence if present in the sample and the reference RNA sequence;
   (iv) measuring the amounts of the amplified selected target viral RNA sequence and the amplified reference RNA sequence; and
   (v) determining the relative amount of the target viral RNA present in the sample before amplification from the amount of the amplified selected target viral RNA sequence and the amount of the amplified reference RNA sequence.

43. A process for quantitation of a target viral RNA sequence in a sample which comprises:
   combining a known quantity of a reference RNA sequence with the sample, wherein the reference RNA sequence comprises a sequence present in the target viral RNA sequence and a sequence not present in the target viral RNA sequence, wherein the reference RNA sequence and the target viral RNA sequence can be amplified by different oligonucleotides and wherein following amplification amplified reference RNA sequence and amplified target viral RNA sequence are distinguishable by size or by probes;
   simultaneously subjecting the target viral RNA sequence and the reference RNA sequence to polymerase chain reaction amplification under conditions appropriate to simultaneously amplify the target viral RNA sequence and the reference RNA sequence;
   measuring the amounts of amplified target viral RNA sequence and amplified reference RNA sequence; and
   determining the relative amount of the target viral RNA sequence present in the sample before amplification from the amount of the amplified target viral RNA sequence and the amount of the amplified reference RNA sequence.

44. A process for quantitation of a target viral RNA sequence in a sample which comprises:
   combining a known quantity of a reference RNA sequence with the sample, wherein the reference RNA sequence comprises a sequence present in the target viral RNA sequence and a sequence not present in the target viral RNA sequence, wherein the reference RNA sequence and the target viral RNA sequence can be amplified by different oligonucleotides and wherein following amplification amplified reference RNA sequence and amplified target viral RNA sequence are distinguishable by size or by probes;
   simultaneously subjecting the target viral RNA sequence and the reference RNA sequence in the sample first to a reverse transcription reaction and then to polymerase chain reaction amplification under conditions appropriate to simultaneously amplify the target viral RNA sequence if present in the sample and the reference RNA sequence;
   measuring the amounts of amplified target viral RNA sequence and amplified reference RNA sequence; and determining the relative amount of the target viral RNA sequence present in the sample before amplification from the amount of the amplified target viral RNA sequence and the amount of the amplified reference RNA sequence.

45. An amplification reaction mixture for the quantitation of a target viral RNA sequence in a biological sample, said reaction mixture comprising:
- a target viral RNA sequence;
- a known quantity of a reference RNA sequence, wherein the reference RNA sequence comprises a sequence present in the target viral RNA sequence and a sequence not present in the target viral RNA sequence, wherein the reference RNA sequence and the target viral RNA sequence can be amplified by different oligonucleotides and wherein following amplification amplified reference RNA sequence and amplified target viral RNA sequence are distinguishable by size or by probes; and
- an oligonucleotide primer pair for each of the target viral RNA sequence and the reference RNA sequence to be amplified.

46. A reverse transcription reaction mixture for reverse transcribing a target viral RNA sequence suspected of being present in a biological sample, said reaction mixture comprising:
- a target viral RNA sequence;
- a known quantity of a reference RNA sequence, wherein the reference RNA sequence comprises a sequence present in the target viral RNA sequence and a sequence not present in the target viral RNA sequence, wherein the reference RNA sequence and the target viral RNA sequence can be amplified by different oligonucleotides and wherein following amplification amplified reference RNA sequence and amplified target viral RNA sequence are distinguishable by size or by probes; and
- an oligonucleotide primer pair for each of the target viral RNA sequence and the reference RNA sequence to be amplified for initiating cDNA synthesis to provide a target viral cDNA and a reference sequence cDNA, whereby following reverse transcription the resulting target viral and reference sequence cDNAs can serve as templates for amplification for providing amplified reference RNA sequence and amplified target viral RNA sequence.

47. A kit for the quantitation of a target viral RNA sequence in a biological sample comprising individual containers which provide:
- a known quantity of a reference RNA sequence, wherein the reference RNA sequence comprises a sequence present in the target viral RNA sequence and a sequence not present in the selected target viral RNA sequence, wherein the reference RNA sequence and the target viral RNA sequence can be amplified by different oligonucleotides and wherein following amplification amplified reference RNA sequence and amplified target viral RNA sequence are distinguishable by size or by probes; and
- an oligonucleotide primer pair for each of the target viral RNA sequence and the reference RNA sequence to be amplified.

* * * * *

UNITED STATES PATENT AND TRADEMARK OFFICE
CERTIFICATE OF CORRECTION

| | |
|---|---|
| PATENT NO. | : 8,227,191 B1 |
| APPLICATION NO. | : 07/402450 |
| DATED | : July 24, 2012 |
| INVENTOR(S) | : George J. Murakawa et al. |

It is certified that error appears in the above-identified patent and that said Letters Patent is hereby corrected as shown below:

*In the Specification*

Col. 4, line 6: "TTA CGC" should be -- TAC TGC --

Signed and Sealed this
Fifteenth Day of January, 2013

David J. Kappos
*Director of the United States Patent and Trademark Office*

UNITED STATES PATENT AND TRADEMARK OFFICE
CERTIFICATE OF CORRECTION

PATENT NO. : 8,227,191 B1
APPLICATION NO. : 07/402450
DATED : July 24, 2012
INVENTOR(S) : George J. Murakawa et al.

It is certified that error appears in the above-identified patent and that said Letters Patent is hereby corrected as shown below:

In the Specification

Column 1, Lines 14-17:
"This invention was made with government support under Grant Nos. U01 CA34991 and P01 CA30206 awarded by the National Institutes of Health. The government has certain rights in the invention."
Should be:
-- This invention was made with government support under U01 CA034991, and P01 CA030206 awarded by the National Institutes of Health. The government has certain rights in the invention. --

Signed and Sealed this
Twenty-third Day of April, 2024

Katherine Kelly Vidal
*Director of the United States Patent and Trademark Office*